United States Patent
Michaelson et al.

(10) Patent No.: US 6,534,000 B1
(45) Date of Patent: Mar. 18, 2003

(54) STERILIZATION CASSETTE AND METHOD

(75) Inventors: Dennis J. Michaelson, Pocatello, ID (US); Jeffrey W. Mix, Burley, ID (US)

(73) Assignee: Steri Source, Inc., Burley, ID (US)

( * ) Notice: Subject to any disclaimer, the term of this patent is extended or adjusted under 35 U.S.C. 154(b) by 0 days.

(21) Appl. No.: 09/560,874

(22) Filed: Apr. 28, 2000

(51) Int. Cl.$^7$ ............................................. A61L 9/00
(52) U.S. Cl. .................. 422/20; 206/363; 206/370; 422/25; 422/26; 422/28; 422/40; 422/297; 422/300
(58) Field of Search ........................... 422/20, 25, 26, 422/28, 40, 297, 300; 206/363, 370

(56) References Cited

U.S. PATENT DOCUMENTS

| | | | |
|---|---|---|---|
| 3,925,014 A | * 12/1975 | Langdon | 206/370 |
| 4,229,420 A | * 10/1980 | Smith et al. | 206/363 |
| 4,327,060 A | 4/1982 | Nisii | 422/300 |
| 4,342,391 A | * 8/1982 | Schainholz | 206/370 |
| 4,541,992 A | 9/1985 | Jerge et al. | 422/300 |
| 4,552,163 A | 11/1985 | Biancalana et al. | 134/100 |
| 4,617,178 A | 10/1986 | Nichols | 422/310 |
| 4,643,303 A | * 2/1987 | Arp et al. | 206/370 |
| 4,661,326 A | 4/1987 | Schainholz | 422/310 |
| 4,671,943 A | 6/1987 | Wahlquist | 422/300 |
| 4,752,444 A | 6/1988 | Bowen et al. | 422/28 |
| 4,774,063 A | 9/1988 | Runnells | 422/297 |
| 4,915,913 A | 4/1990 | Williams et al. | 422/119 |
| 4,971,774 A | 11/1990 | Schwanke et al. | 422/310 |
| 5,039,495 A | 8/1991 | Kutner et al. | 422/299 |
| 5,176,884 A | 1/1993 | Taschner et al. | 422/292 |
| 5,184,046 A | 2/1993 | Campbell | 315/111.21 |
| 5,215,726 A | 6/1993 | Kudla et al. | 422/297 |
| 5,340,551 A | * 8/1994 | Berry, Jr. | 206/363 |
| 5,346,677 A | * 9/1994 | Risk | 206/363 |
| 5,372,787 A | 12/1994 | Ritter | 422/119 |
| 5,407,354 A | * 4/1995 | Fife | 206/438 |
| 5,411,136 A | * 5/1995 | Brigham | 206/459.5 |
| 5,449,069 A | * 9/1995 | Pijanowski et al. | 206/370 |
| 5,480,302 A | 1/1996 | Fife | 433/116 |
| 5,482,067 A | 1/1996 | Wittrock et al. | 134/135 |
| 5,543,119 A | 8/1996 | Sutter et al. | 422/299 |
| 5,641,065 A | 6/1997 | Owens et al. | 206/370 |
| 5,743,734 A | 4/1998 | Heath et al. | 433/77 |
| 5,759,502 A | 6/1998 | Spencer et al. | 422/300 |
| 5,858,303 A | 1/1999 | Schiffmann et al. | 422/21 |
| 5,871,702 A | 2/1999 | Kutner et al. | 422/299 |
| 5,918,740 A | * 7/1999 | Berry, Jr. | 206/369 |
| 5,961,937 A | 10/1999 | Gobbato | 422/300 |
| 6,010,670 A | 1/2000 | Berry, Jr. | 422/295 |
| 6,113,867 A | * 9/2000 | Mayer | 206/369 |

* cited by examiner

*Primary Examiner*—Krisanne Thornton
(74) *Attorney, Agent, or Firm*—Robert L. Shaver; Frank J. Dykas; Stephen M. Nipper

(57) ABSTRACT

A sterilization cassette and a sterilization method for sterilizing, storing, and dispensing dental instruments. The sterilization cassette includes a mounting bar and a locking bar for dental pliers of various types, a removable instrument tray, and a case with a front side which opens and hinges in two places, allowing the cassette to be arranged in horizontal and vertical configurations.

14 Claims, 7 Drawing Sheets

STERILIZATION CASSETTE AND METHOD

BACKGROUND OF THE INVENTION

1. Field of the Invention

The present invention generally relates to a cassette and tray system wherein cassettes of varying sizes are used to hold collections of orthodontic or dental tools for use in the sterilization process.

2. Background Information

While the human mouth is hardly a sterile environment, there is a need to protect patients from the transmission of infectious diseases from one patient to another through the use of contaminated orthodontic or dental tools. Gone are the days when the orthodontist or dentist merely washed his hand tools between use on patients. Such organizations as the American Dental Association, American Association of Orthodontics, the Federal Occupational Safety and Health Administration and the Center for Disease Control are all actively working to set standards and guidelines to insure the safety of the patients as well as the orthodontists, dentists, and their assistants.

At the present time, there are three standardized methods of sterilizing dental and orthodontic hand tools. In each of the three, the hand tools are first dropped into a tank containing water and perhaps solvents, and ultrasound is applied to agitate the fluid to wash and remove the debris remaining on the hand tools from their last use. The tools are left somewhat damp then dried and heated in some manner to a temperature sufficient to destroy any microorganisms or viruses on the hand tools. The three primary methods of doing this are the use of dry heat, heat wherein the hand tools are heated to a temperature of at least 365° Fahrenheit for six minutes, or the use of steam under pressure in an autoclave system. The time to sterilize, using a steam autoclave system, depends on heat and pressure and whether the instruments are wrapped or not. A common wrapped cycle is 270° at 27 psi for fifteen minutes. An unwrapped cycle at the same temperature and pressure would be for three minutes. In some sterilization processes, chemicals are applied to the hand tools as an intermediate step between the ultrasonic bath and the heating. A third method of sterilization is a chemical clave wherein a heated, controlled atmosphere of various gases is used to heat the hand tools held within sealed sterile paper bags.

The problem is that orthodontists and dentists with busy professional practices will see many patients in any given work day, indeed it is not unusual for an orthodontist to see in excess of 100 patients per day. A lot of hand tools are used each day, and they are generally collected throughout the day and recycled, in bulk, through the sterilization process. In a busy orthodontics practice, it is not unusual to have one assistant dedicated solely to collecting hand tools and sterilizing them on a full time basis.

In the typical prior art orthodontic or dental practice, once the tools have been resterilized, they are simply returned to the work station and placed where they are readily available for reuse. However, this is a source of contamination. If, for example, a dentist is working on a patient's teeth and calls to his assistant for a new and different tool, and the assistant reaches into the drawer to retrieve the tool wearing a latex glove that has been contaminated with the body fluids of the patient, the assistant can transfer those contaminants to other, unused tools which were previously sterilized. Inevitably, conditions arise where contaminated hands are used to retrieve tools from the drawers.

Accordingly, what is needed is a cassette system wherein cassettes can be preloaded with standard sets of tools for use in either orthodontic or dental practices, and kept together as a set throughout the sterilization process. What is also needed is a means of collecting the cassettes into convenient packages where they can be batch fed through the ultrasonic bath and heat applications, and remain in a sterile condition when they are returned as a set to the work station. Another need is for a sterilization cassette in which dental pliers and dental instruments can be carried through the sterilization process in a sterilization cassette which secures dental pliers in place during the sterilization process. The sterilization cassette also needs to be usable as a storage container, and be convertible into a dispensing device which dispenses the dental pliers and dental instruments from either a horizontal or a vertical position. Additionally, this cassette collection system must require a minimum amount of counter space at the vicinity of the dental chair, either on the bracket table or the work side unit, and finally, the cassettes must be configured such that they remain stable and flat on the countertop surface when opened so that they do not fall off the table onto the floor, or worse yet, the patient.

Additional objects, advantages and novel features of the invention will be set forth in part in the description as follows, and in part will become apparent to those skilled in the art upon examination of the following, or may be learned by practice of the invention. The objects and advantages of the invention may be realized and attained by means of the instrumentalities and combinations particularly pointed out in the appended claims.

SUMMARY OF THE INVENTION

These objects are achieved through use of a transfer rack and a plurality of cassette systems. The transfer rack is formed of side walls, a back wall, and a bottom wall which are all interconnected to form a rigid transfer rack. The tray is provided with a plurality of shelves for holding cassettes which are inserted through the front of the transfer rack. The walls and shelves of the transfer rack are provided with a plurality of holes or slots through which fluids and debris cleaned during the ultrasonic cleaning portion of the sterilization process may readily pass.

The transfer rack is also provided with two flanges which are attached to the top of the side walls. The transfer rack is dimensionally sized to a preselected dimension as to provide for interchangeability of cassettes as is later described.

The sterilization cassette for dental pliers and dental instruments is a generally rectangular case. It has a back side, a front side, a left side, a right side, a top side, and a bottom side. The case opens by the front side hinging forward. To the front side, which hinges forward, is attached the top side, and portions of the left and right side. At least one of the sides of the sterilization cassette contains perforations which allow for the passage of sterilization gases through the cassette.

A plier mounting bar is attached to the left side and the right side, and extends through the cassette from these sides. Dental pliers are placed on the plier mounting bar. The plier mounting bar is divided into two or more dividers, which provide each dental plier a discreet position on the plier mounting bar. A plier locking bar is provided which attaches to the front side. When the front side swings to its closed position, the plier locking bar presses against the dental pliers on the plier mounting bar, and holds them in place. One or more removable instruments trays is also provided. Other dental instruments can be placed in the instrument tray for passage through the sterilization process. The sterilization cassette is configured so that it may serve as a storage container for the dental pliers or dental instruments, and it also may be used as a dispensing tray which is positionable in either a horizontal or vertical position, for dispensing these tools when a dentist works with a patient.

In another version of the invention, the metal case opens by two hinges which are located on the front side. The first and second hinge on the front side divide the front side into a bottom front side, a mid front side, and a top front side. The top front side is attached to the first hinge. The top side is also attached to the top front side, and part of the left and right side is also attached to the top front side. The second hinge divides the mid front side from the top front side, and allows further opening of the front side to make the dental pliers and dental instruments accessible.

Another aspect of the invention is a method of sterilizing, storing, and dispensing dental pliers and dental instruments. This method involves the steps of providing one of the sterilization cassettes previously described, and placing dental pliers on the plier mounting bar. The pliers are placed between plier mounting bar dividers, and dental instruments are also placed in one of the removable metal instruments trays. The next step is closing the sterilization cassette, so that the plier locking bar presses down on the dental pliers and holds them firmly in place on the plier mounting bar. The cassette may be placed in a transfer rack, or may be placed in an ultrasound cleaning chamber without a transfer rack. After a period of time in the ultrasonic cleaning chamber, the cassette is removed from the ultrasonic cleaning chamber, and the fluid from the ultrasonic cleaning chamber is drained from the cassette, without opening the cassette. At this point, the cassette may optionally be placed inside a membrane which is permeable to sterilization gases but is impermeable to microbes. The sterilization cassette is then placed in a sterilization chamber. The sterilization chamber can be any of the conventionally available sterilization chambers, which utilize heat, steam, chemical vapors, pressure, or combinations of any of these. After sterilization is complete, the sterilization cassette is removed from the sterilization chamber and allowed to cool to ambient temperature. The sterilization cassette is then used as the storage container of the dental pliers and dental instruments, and may be placed in an appropriate storage shelf or housing. When the dental tools within the sterilization chamber are needed for use, the sterilization cassette can be placed in either the vertical or horizontal position, the front side may be opened, and dental pliers and dental instruments may be dispensed.

The cassettes are also provided with color coded markers fixed to the end walls and plier mounting bar so that the kits of dental tools that are contained within each cassette and the individual dental tools can be readily identified.

Still other objects and advantages of the present invention will become readily apparent to those skilled in this art from the following detailed description wherein I have shown and described only the preferred embodiment of the invention, simply by way of illustration of the best mode contemplated by carrying out my invention. As will be realized, the invention is capable of modification in various obvious respects all without departing from the invention. Accordingly, the drawings and description of the preferred embodiment are to be regarded as illustrative in nature, and not as restrictive.

DESCRIPTION OF THE PREFERRED EMBODIMENTS

Figure 1:
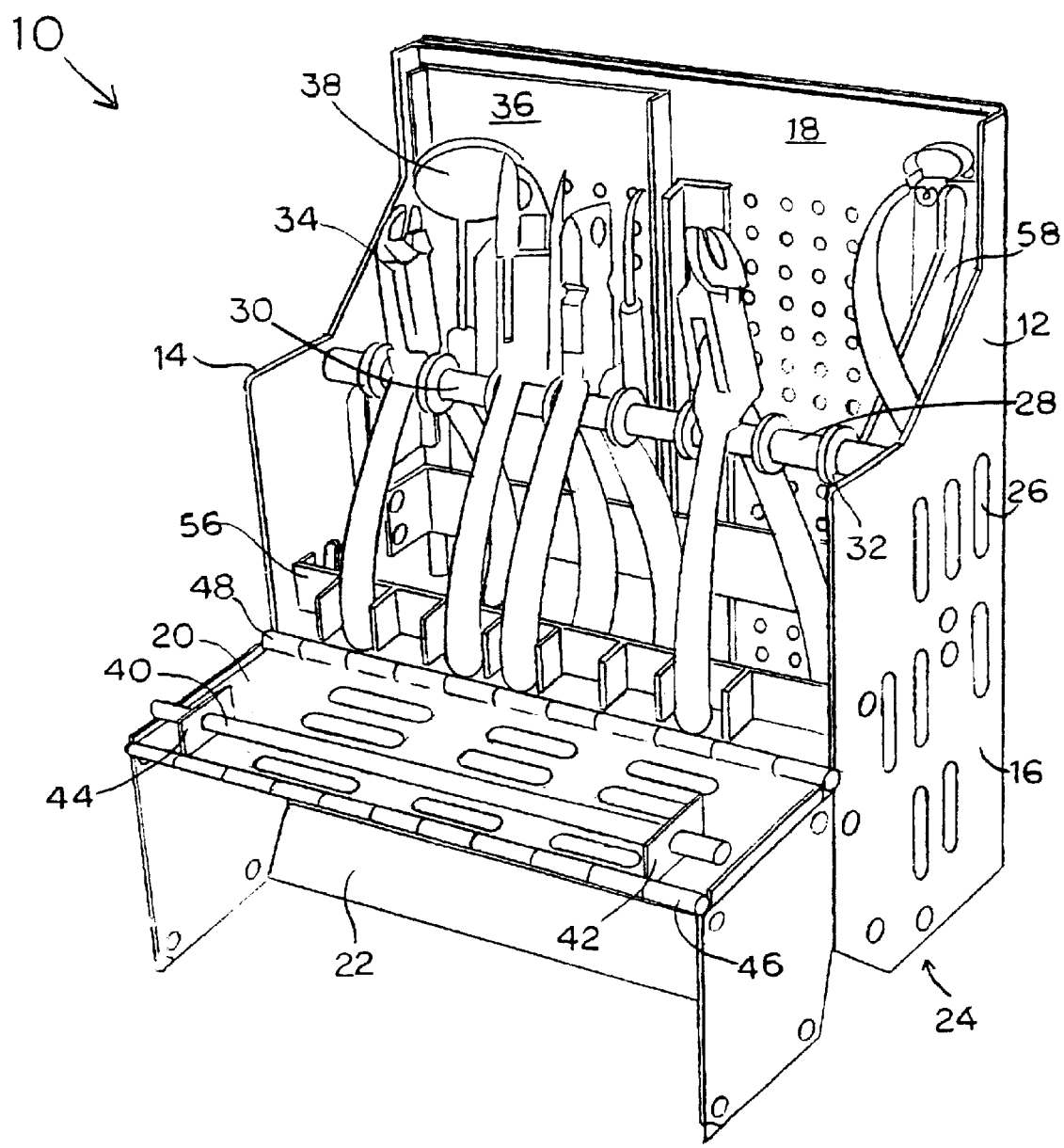
FIG. 1 is a perspective representational view of the sterilization cassette configured for dispensing tools in a vertical position.

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

Some of the preferred embodiments of the invention are shown in FIGS. 1 through 7. Referring to FIG. 1, there is shown a sterilization cassette 10. Sterilization cassette 10 includes a generally rectangular case 12 which is preferably made of metal such as stainless steel. Other materials which are suitable to withstand the ultrasonic cleaning and sterilization process would also be acceptable to use in case 12, such as other metals, plastics, ceramics, or other materials. Case 12 includes a left side 14, a right side 16, a back side 18, a front side 20, a top side 22, and a bottom side 24. In the preferred embodiment of the invention shown in FIG. 1, each of these sides have perforations 26, which allow the passage of hot air, steam, ultrasonic cleaning fluid, and sterilization chemical vapors into and out of the sterilization cassette 10.

The case 12 includes a plier mounting bar 28 which extends from right side 16 to left side 14. Plier mounting bar 28 would typically be a metal bar covered by Teflon® cylinders 30. The Teflon® cylinders 30 would preferably be color coded to allow fast identification of dental pliers, and accurate replacement in the rack after use. The Teflon® cylinders 30 are separated by metal disks 32, which form individual positions for dental pliers 34. Dental pliers 34 can include a number of plier-like instruments, and specifically include hard wire cutters, bird's beak pliers, three-prong pliers, ligature cutters, adjustment pliers, Weingart pliers, hemostats, and other plier-like dental hand tools. An instrument tray 36 is also provided, and other small dental instruments 38 are placed in instrument tray 36. Dental instruments 38 can include a number of instruments such as mirrors, picks, scrapers, files, scalpels, and other small hand tools. The Teflon® cylinders 30 and the metal disks 32, form plier mounting positions.

Figure 5:
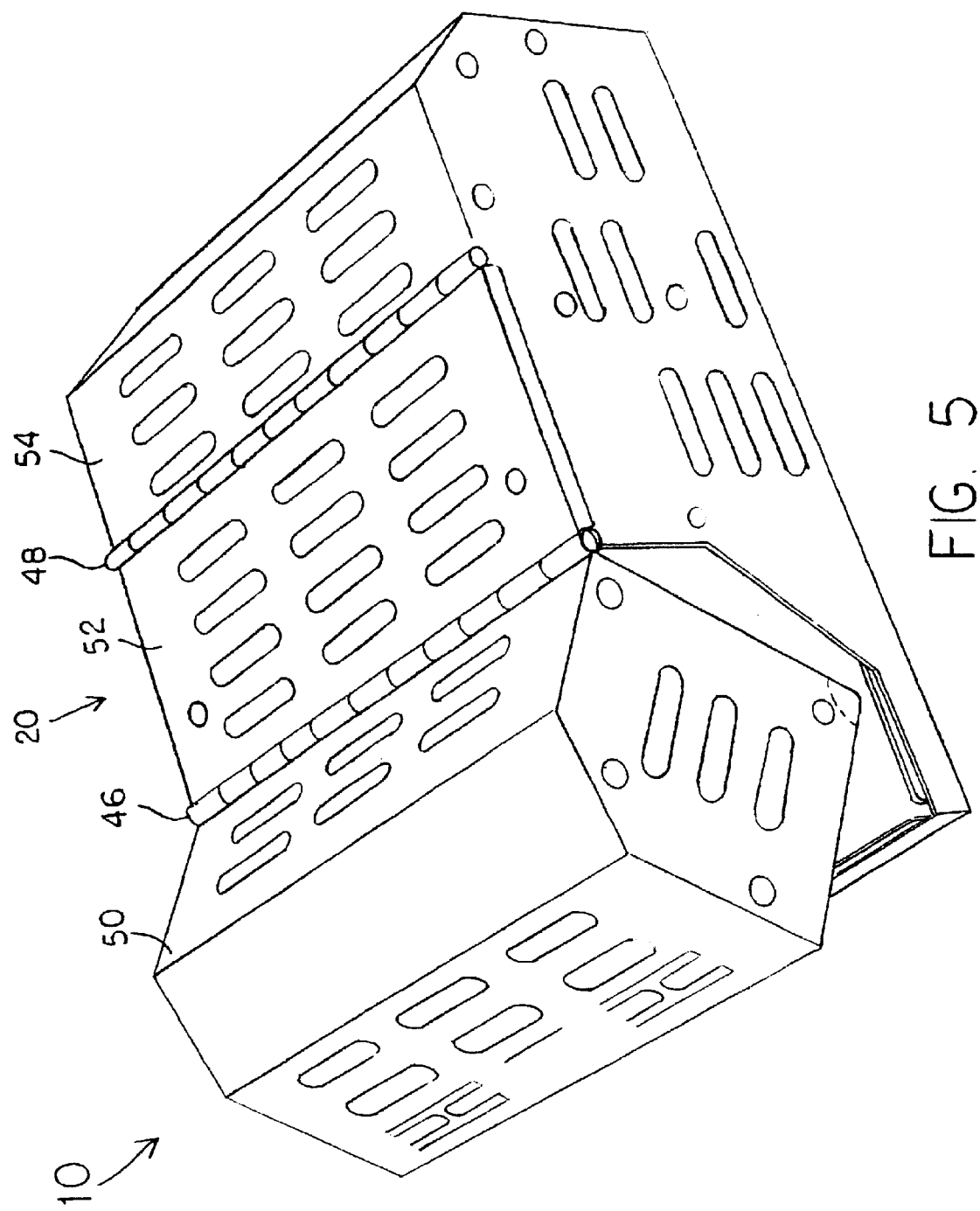
FIG. 5 is a perspective representational view of the sterilization cassette showing the cassette almost closed.

The sterilization cassette 10 also includes a plier locking bar 40 which is attached to front side 20 of case 12. Plier locking bar 40 is a bar which extends from a first bracket 42 to a second bracket 44, each of which is attached to front side 20. Plier locking bar 40 would typically be a metal bar which is covered by a Teflon® covering. In a preferred embodiment of the invention, case 12 includes a first hinge 46 and a second hinge 48. In this embodiment of the invention, first hinge 46 and second hinge 48 are piano hinges and divide front side 20 into three portions. These portions are best seen in FIG. 5. First hinge 46 divides front cover 20 into a top front side 50 and a mid front side 52. Second hinge 48 divides front cover 20 into another side, a bottom front side 54.

Referring again to FIG. 1, sterilization cassette 10 further includes plier handle divider 56. Sterilization cassette 10 also includes a tool slot 58, into which larger tools such as hemostats or forceps may be placed for sterilization.

By utilizing the double hinge configuration of sterilization cassette 10, sterilization cassette 10 may be configured in a number of ways to suit the needs of the user. FIG. 1 shows sterilization cassette 10 arranged in a vertical configuration, so that dental pliers 34 or dental instruments 38 may be removed or replaced in their positions in a horizontal configuration.

Figure 2:
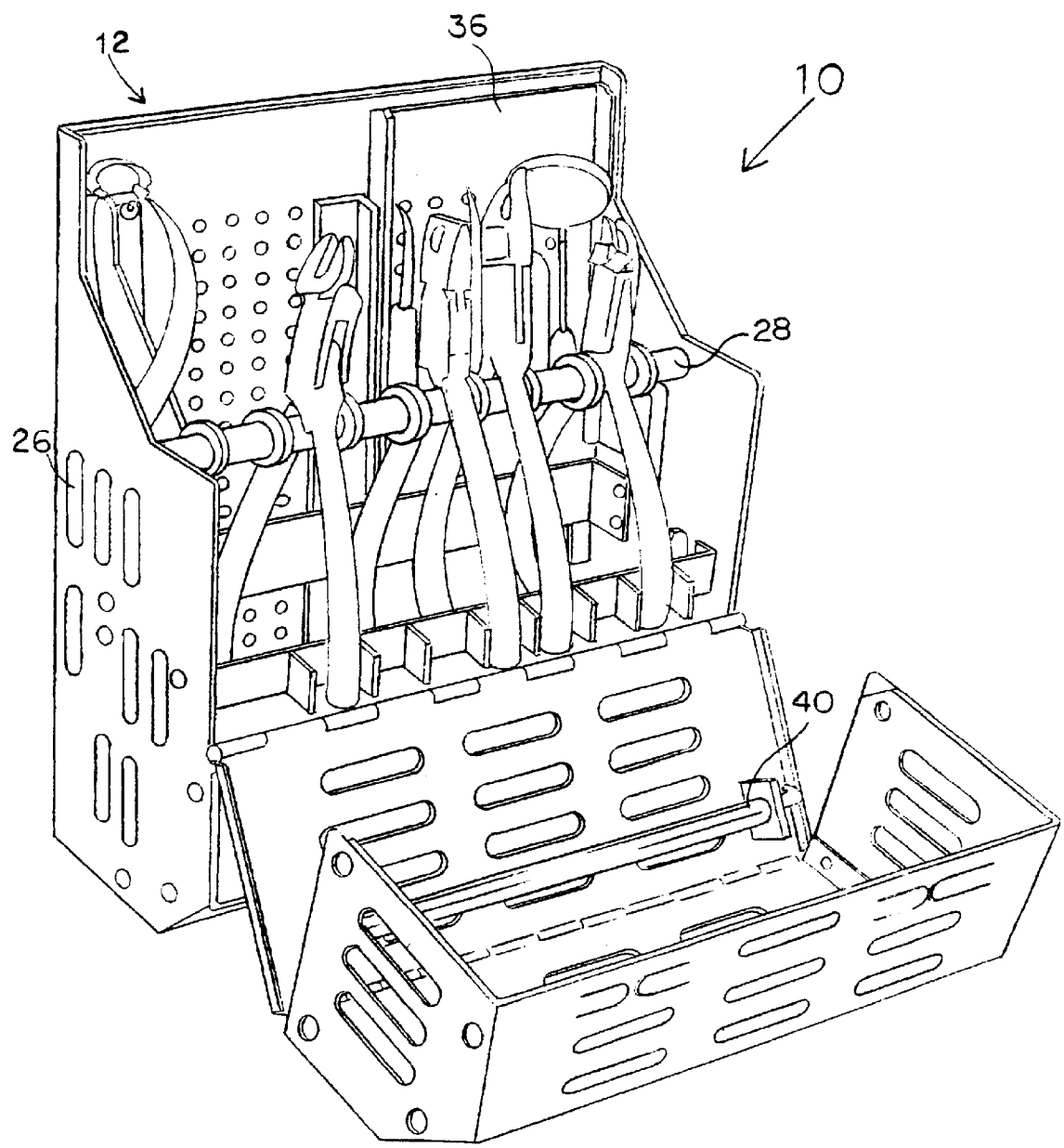
FIG. 2 is a perspective representational view of the sterilization cassette configured for dispensing tools in a vertical position, with the hinging front cover and top arranged to form a storage area.
Figure 3:
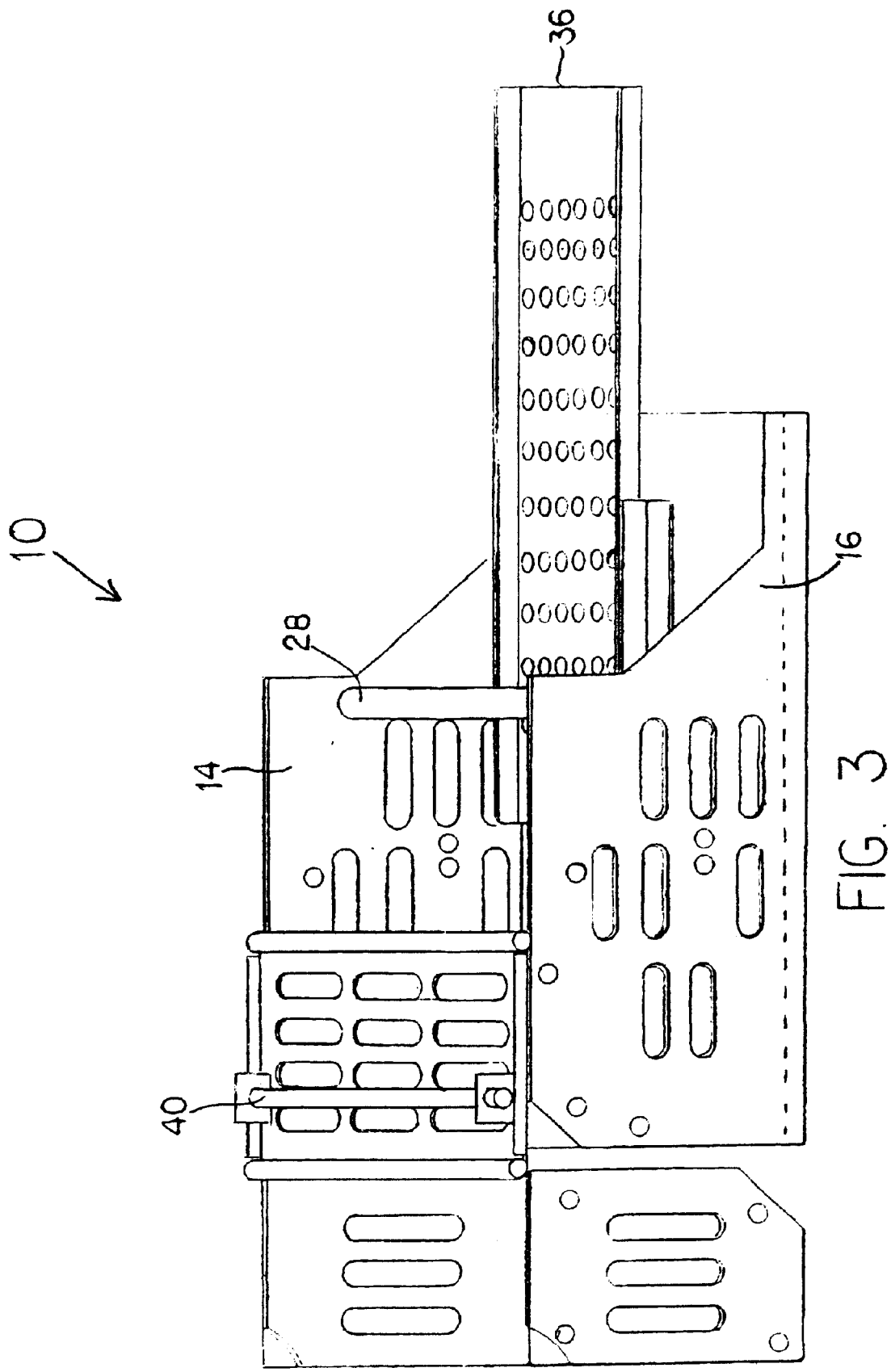
FIG. 3 is a side view of the sterilization cassette configured for horizontal dispensing or loading of tools.
Figure 4:
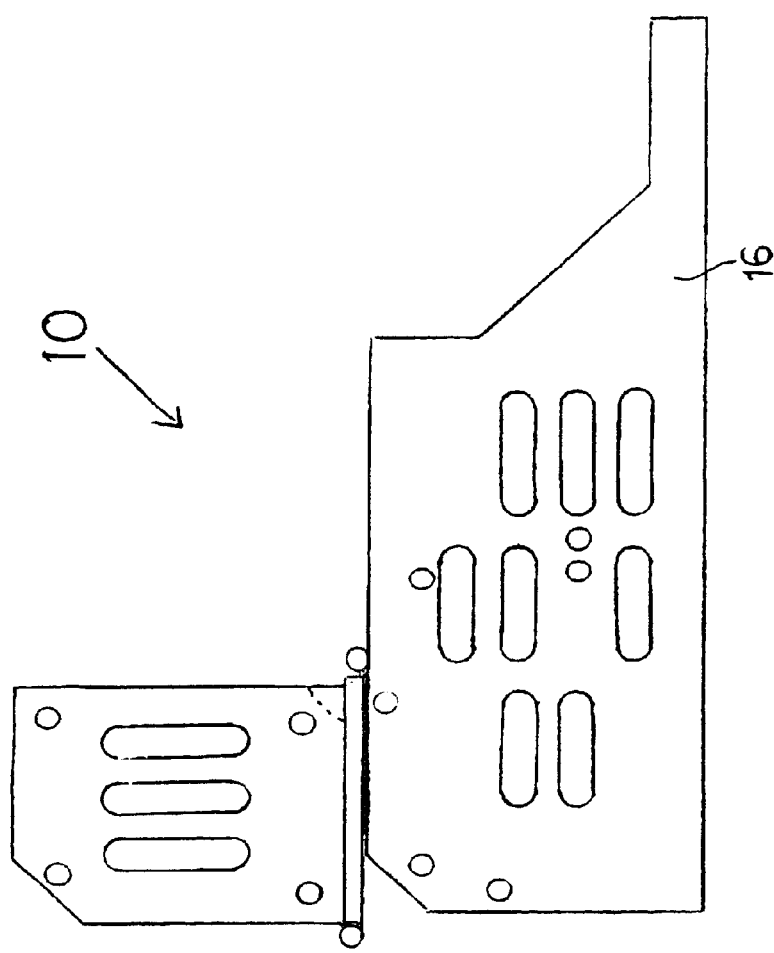
FIG. 4 is a side view of the sterilization cassette in a horizontal configuration, with the opening front cover and top side arranged to form a storage compartment on the sterilization cassette.

FIG. 2 shows sterilization cassette 10 in a vertical configuration, with front side 20 folded into a configuration which provides a tray below the tools of the open cassette. FIG. 3 shows the sterilization cassette 10 in horizontal configuration, and in this configuration, tools would be presented to the practitioner in a horizontal rather than a vertical format. In the horizontal configuration, the front side 20 can also be folded to various configurations. One configuration is shown in FIG. 3, and another configuration of front side 20 is shown in FIG. 4.

FIG. 5 shows the sterilization cassette 10 in an almost closed configuration, in which top front side 50 is open only slightly.

Figure 6:
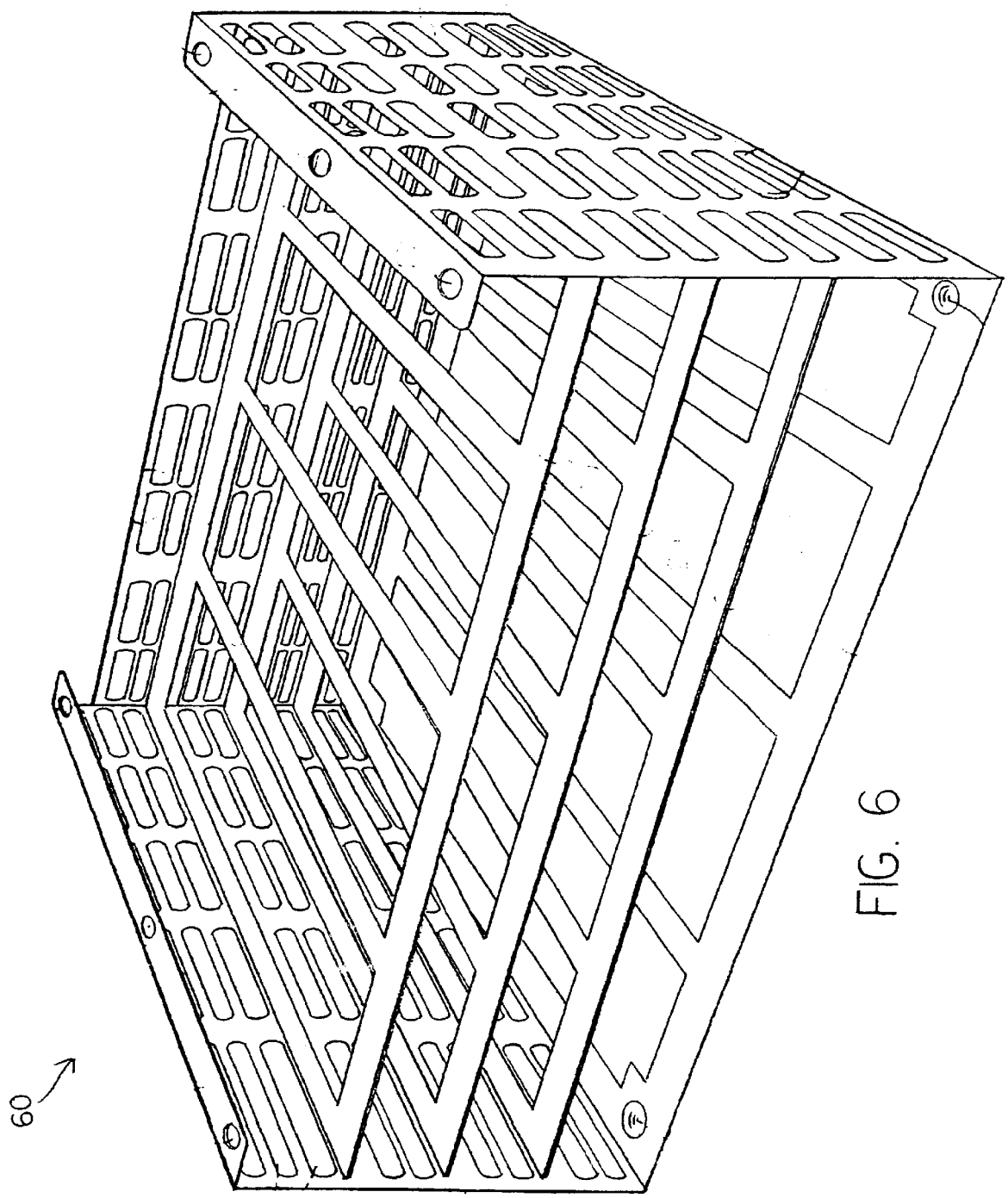
FIG. 6 is a view of the transfer rack of the sterilization method.
Figure 7:
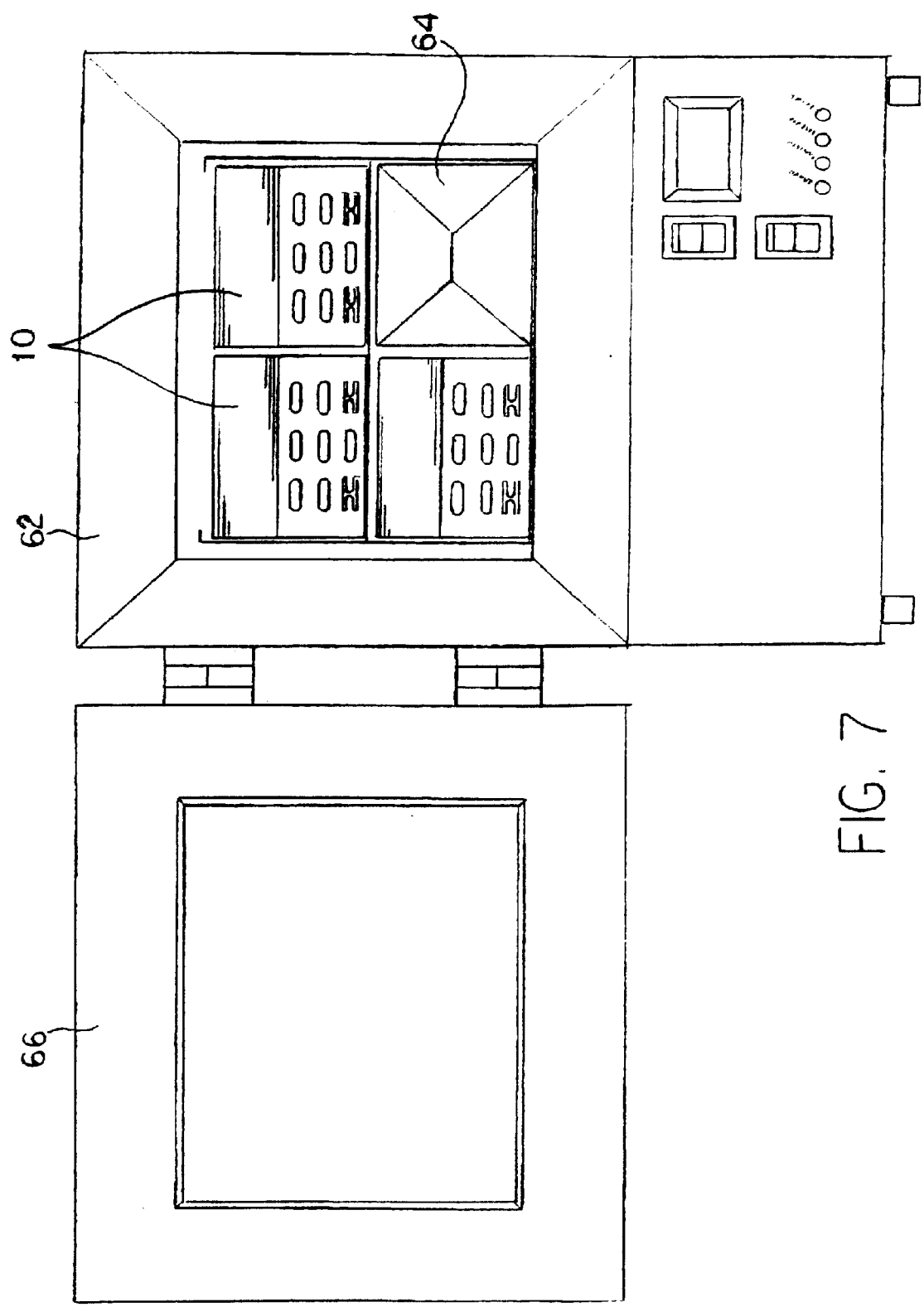
FIG. 7 is a front view of a number of sterilization cassettes mounted on a transfer rack placed in a sterilization chamber, with one of the sterilization cassettes wrapped in a membrane.

FIG. 6 shows a transfer rack 60. This particular transfer rack is configured with four trays, and the number of trays would vary according to the size of the sterilization oven. A typical sterilization oven is shown in FIG. 7, and includes a transfer rack 60 with four sterilization cassettes 10. In FIG. 7, one of the sterilization cassettes 10 is shown wrapped in a membrane 64. One option for sterilizing instruments in the sterilization cassettes 10 is to cover the sterilization cassettes 10 with a membrane 64 which allows the passage of gases, which is stable in the heat in the sterilization chamber, and which is impermeable to microbes. A membrane 64 could be folded around a sterilization cassette 10, much like the wrapping of a gift. The membrane 64 could also be in the form of a bag with a sealable closure. The oven shown in FIG. 4 is similar to a popular type of sterilization oven such as the Dentronix 5000. There are a number of configurations of sterilization cassettes, some of them with polygonal chambers, and transfer rack 60 can be adapted for different sizes and configurations of sterilization ovens 62. FIG. 7 shows sterilization oven 62 with the oven door 66 open.

While there is shown and described the present preferred embodiment of the invention, it is to be distinctly understood that this invention is not limited thereto but may be variously embodied to practice within the scope of the following claims.

From the foregoing description, it will be apparent that various changes may be made without departing from the spirit and scope of the invention as defined by the following claims.

We claim:
1. An instrument sterilizing cassette comprising:
  a generally rectangular case, made of a heat resistant material having a back side front side, left side, right side, a top side, and a bottom side, all interconnected in which a portion of said case including said top side and part of said front side, a part of said left side and a part of said right side opens by a hinging means, and in which at least one of said sides defines perforations for passage of sterilization gasses;
  a plier-mounting bar for mounting dental pliers attached parallel to said front side;
  a plurality of plier mounting bar dividers on said plier mounting bar, for mounting dental pliers in said sterilizing cassette;
  a plier-locking bar attached to said front side, for holding said dental pliers in place on said mounting bar when said sterilizing cassette is closed;
  one or more removable metal instrument trays for holding dental instruments in said sterilizing cassette for sterilization; wherein
  said sterilizing cassette is configured for dispensation of dental pliers or dental instruments from either a horizontal or a vertical position.

2. The instrument sterilizing cassette of claim 1 in which said metal case opens by a first and a second hinge in said front side, and in which said two hinges divide said front side into a bottom front side, a mid front side, and a top front side, in which said top front side is attached to said first hinge, and opens at said first hinge and is attached to said top side, and part of said front side, and part of said front side, and said mid front side opens further at said second hinge.

3. The instrument sterilizing cassette of claim 1 in which said plier locking bar is attached to said front side.

4. The instrument sterilizing cassette of claim 2 in which said plier locking bar is attached to said mid front side.

5. The instrument sterilizing cassette of claim 4 in which said plier locking bar is a Teflon® cylinder.

6. The instrument sterilizing cassette of claim 1 in which said metal case is configuired to allow both storage and dispensing of dental and orthodontic tools therefrom.

7. The instrument sterilizing cassette of claim 1 in which said plier mounting bar is color coded to identify positions on said plier mounting bar for specific dental pliers which are correspondingly color coded.

8. A method of sterilizing, storing, and dispensing dental pliers and dental instruments, which comprises the steps of:
  providing a heat resistant sterilization cassette, in which the said sterilization cassette comprises a generally rectangular metal case, having a back side, a front side, a left side, a right side, a top side, and a bottom side, wherein a portion of said rectangular case including said top side and part of said front side opens by hinging, and wherein said sides define perforations for passage of gases for sterilization, and wherein said sterilization cassette further comprises a plier mounting bar for mounting dental pliers, a plurality of plier mounting bar dividers on said plier mounting bar, for mounting dental pliers in said sterilizing cassette, a plier locking bar attached to said front side, for holding said dental pliers in place when said sterilizing cassette is closed, one or more removable metal instrument trays, for holding dental instruments in said sterilizing cassette for sterilization, wherein said sterilizing cassette is adapted for dispensation of dental pliers or dental instruments from either a horizontal or a vertical position;

placing dental pliers on said plier mounting bar, between plier mounting bar dividers, and placing dental instruments in said one or more removable metal instrument trays;

closing said sterilization cassette, so that said plier locking bar presses down on said dental pliers and firmly holds said dental pliers in place on said plier mounting bar;

placing said sterilization cassette in an ultrasound cleaning chamber, for ultrasonic cleaning of said dental pliers and said dental instruments;

removing said sterilization cassette from said ultrasound cleaning chamber;

placing said sterilization cassette in a sterilization chamber;

sterilizing said sterilization cassette in said sterilization chamber;

removing said sterilization cassette from said sterilization chamber, and allowing said sterilization cassette to cool to ambient temperature;

storing said sterilization cassette until said dental pliers and dental instruments are needed; and placing said sterilization cassette in either a vertical or horizontal position for dispensation of dental pliers and dental instruments.

9. The method of sterilizing, storing, and dispensing dental pliers and dental instruments of claim 8, which comprises the step of placing said sterilization cassette in a gas permeable and microbe impermeable membrane after said ultrasound cleaning step, sealing said membrane, and leaving said membrane on said sterilization cassette until dispensation of said dental pliers and dental instruments.

10. The method of sterilizing, storing, and dispensing dental pliers and dental instruments of claim 9 in which said membrane is a planar unit of membrane material which is folded and secured around said sterilization cassette.

11. The method of sterilizing, storing, and dispensing dental pliers and dental instruments of claim 9 in which said membrane is a sealable flexible container.

12. The method of sterilizing, storing, and dispensing dental pliers and dental instruments of claim 8, which further comprises the step of placing one or more of said sterilization cassettes on a on transfer rack before said step of placing said sterilization cassette in said ultrasonic cleaning chamber, and moving said sterilization cassette on said transfer rack into and out of said sterilization chamber.

13. The method of sterilizing, storing, and dispensing dental pliers and dental instruments of claim 12 which further includes the step of placing four sealed membranes with enclosed sterilization cassettes on a transfer in a sterilization chamber.

14. A system for organizing, sterilizing, and dispensing dental instruments and tools comprising:

a transfer rack made of a heat resistant material and having at least two layers dimensioned to receive a plurality of instrument sterilizing cassettes therein, said transfer rack configured for placement within a sterilizing environment and having a plurality of perforations therein to allow passage of sterilizing materials and debris;

each of said instrument sterilizing cassettes configuired for placement within said transfer rack and further configured for aseptically dispensing dental pliers and dental instruments from either a horizontal or a vertical position each of said cassettes comprising:

a generally rectangular case, having a back side, front side, left side, right side, a top side, and a bottom side all interconnected and defining therein an inner sterilization chamber, access to said inner sterilization chamber is provided through a hinged access portal wherein a first and a second hinge in said front side divide said front side into a bottom front side, a mid front side, and a top front side, wherein said top front side is attached to said first hinge and opens at said first hinge said first hinge also attached to said top side, said top side also attached to a portion of said left side and said right side, said top front side also connected to said mid front side by said second hinge, said second hinge also connected to said bottom portion of said front side, at least one of said sides defining perforations for passage of sterilization gasses; a generally cylindrical plier mounting bar for mounting dental pliers located within inner sterilization chamber and attached parallel to said front side; a plurality of plier mounting bar dividers on said plier mounting bar, for mounting dental pliers in said sterilizing cassette; a plier locking bar attached to said mid front side within said inner chamber, for holding said dental pliers in place upon said mounting bar when said sterilizing cassette is closed; a tool slot defined within said inner chamber for accepting and holding tools; a coding system attached to said cassette for indentifying the contents of said cassette; and for designating the location of said tools within said cassette; one or more removable transfer metal instrument trays each tray coded and configuired for holding dental instruments in said sterilizing cassette for sterilization; and a heat stable, microbe impermeable membrane which allows passage of gasses therethrough.

* * * * *